United States Patent [19]

Ranucci

[11] 4,259,323

[45] Mar. 31, 1981

[54] POTASSIUM CHLORIDE EMULSION

[75] Inventor: Joseph A. Ranucci, North Caldwell, N.J.

[73] Assignee: Hoffmann-La Roche Inc., Nutley, N.J.

[21] Appl. No.: 133,184

[22] Filed: Mar. 24, 1980

[51] Int. Cl.$^3$ .................. A61U 31/00; A61U 31/14; A61U 31/365; A61U 31/685

[52] U.S. Cl. .................. 424/153; 424/172; 424/199; 424/280

[58] Field of Search ............... 424/153, 172, 199, 280

[56] References Cited

U.S. PATENT DOCUMENTS

| | | | |
|---|---|---|---|
| 3,821,368 | 6/1974 | Reynolds | 424/153 |
| 3,903,255 | 9/1975 | Gusman et al. | 424/153 |

OTHER PUBLICATIONS

J. Soc. Cosmet. Chem., 28, 284–314 (5–77).
Relaba Technica. 4, 269–282 (1972).
Emulsification of Basic Cosmetic Ingredients, ICI Inc., Wilmington, Del. (1975).

*Primary Examiner*—Stanley J. Friedman
*Attorney, Agent, or Firm*—Jon S. Saxe; George M. Gould; William H. Epstein

[57] ABSTRACT

An improved potassium chloride emulsion having an acceptable taste is disclosed. The disclosed emulsion is a water-in-oil emulsion comprising, per liter, 500 to 700 ml. water, 8 percent to 24 percent weight to volume sorbitol, 100 to 300 ml. of an edible, non-polar oil, 5 percent to 15 percent by weight potassium chloride, 1 percent to 5 percent weight to volume purified bentonite, 10 to 30 ml. of one or a mixture of edible liquid, non-polar esters of unsaturated fatty acids, 0.01 percent to 1.0 percent weight to volume polysorbate 80, and 0 percent to 3 percent by weight lecithin and 0 percent to 5 percent by weight ascorbyl palmitate with suitable, pharmaceutically acceptable preservatives, flavors and sweetening agents.

7 Claims, No Drawings

POTASSIUM CHLORIDE EMULSION

BACKGROUND OF THE INVENTION

It is well recognized that abnormally low levels of potassium chloride in the body may be caused by certain disease states or the administration of certain therapeutic agents, such as, for example, corticosteroids or thiazide-type diuretics. The symptoms of this condition, hypokalemia, include muscular weakness and cardiac disturbances. Treatment of this condition normally comprises replacement of the potassium ion. In view of the fact that therapy with therapeutic agents such as those mentioned above may often be on a prolonged basis, it is often the case that potassium chloride replacement thereapy must be maintained over extended periods of time.

The art is appraised of problems inherent with the administration of potassium chloride. Potassium chloride has been found to be irritating to the gastric mucosa and, therefore, be a potential source of ulceration. This has been shown to be true, for example, with enteric-coated potassium chloride tablets which have caused lesions of the lower bowel over a period of time in all probability due to irritation caused by the concentration of potassium chloride at the sites in the intestinal wall where such tablets dissolve.

There have been numerous attempts to formulate potassium chloride into dosage forms designed to overcome problems such as that described above with varying degrees of success. One approach to the formulation of potassium chloride is to compound it into a liquid formulation. Such a preparation would, for example, be advantageous in that it would be relatively free from the areas of irritation caused by high concentration of potassium chloride at the site of dissolution of a tablet in the stomach or intentinal tract. A second obvious advantage of such liquid preparations would be acceptance by those patients who have difficulty swallowing a tablet.

However, liquid preparations containing potassium chloride can themselves be irritating and, therefore, can cause undesirable effects, such as nausea, diarrhea and gastric upset. The most significant disadvantage of liquid potassium chloride preparations known heretofore is that, regardless of the type of liquid preparation or formulation thereof, such preparations do not have an acceptable taste. It is significant that attempts to date to market a liquid form of potassium chloride have not fared particularly well in comparison with commercial tablets due in the main to the inability of such preparations to mask the salty, objectionable taste of potassium chloride.

The present invention is concerned with a novel water-in-oil emulsion which has been found to efficiently mask the taste of potassium chloride, as well as minimizing the potential irritation of potassium chloride in the gut. The fact that these objectives have been realized utilizing a water-in-oil emulsion is considered unexpected, since water-in-oil emulsions are generally utilized in the health care field only for topical cosmetic preparations, such as cold creams, cleansing creams and the like. Currently, there are no orally administered water-in-oil pharmaceutical products on the market. This may be due to the fact that, in past years, those skilled in the art have generally considered water-in-oil emulsions less stable than oil-in-water emulsions. It has been found, however, in accordance with the present invention that a water-in-oil emulsion can be prepared which effectively masks the objectionable taste of potassium chloride and which has acceptable stability even in the presence of very high electrolyte levels which tend to destabilize most emulsions using conventional emulsifiers.

DETAILED DESCRIPTION OF THE INVENTION

In accordance with the present invention a liquid preparation of potassium chloride is provided which is non-irritating, non-ulcerogenic, possesses good bioavailability and which effectively masks the taste of potassium chloride.

The improved liquid potassium chloride preparation of the present invention is a water-in-oil emulsion which has been found, in addition to the advantages mentioned above, to possess acceptable stability. It has been found that, in consideration of the large number of the adjuncts recognized in the art of pharmaceutical compounding, only certain such ingredients combined in particular ratios will achieve the objectives and advantages of the subject preparations and effectively mask the taste of potassium chloride.

The improved water-in-oil emulsion of potassium chloride provided in accordance with the present invention comprises, per liter, from about 500 ml. to about 700 ml. preferably about 600 ml. water, from about 8 percent weight to volume to about 24 percent weight to volume, preferably about 16 percent weight to volume sorbitol, from about 100 ml. to about 300 ml., preferably about 200 ml. of an edible, non-polar oil, from about 5 percent by weight to about 15 percent by weight, preferably about 10 percent by weight potassium chloride, from about 1 percent weight to volume to about 5 percent weight to volume, preferably about 1 percent weight to volume purified bentonite, from about 10 ml. to about 30 ml. preferably about 20 ml. of one or a mixture of edible liquid, non-polar esters of unsaturated fatty acids, from about 0.01 percent weight to volume to about 1.0 percent weight to volume, preferably about 0.3 percent weight to volume polysorbate 80, from about 0 percent by weight to about 3 percent by weight, preferably about 0.5 percent by weight lecithin, from about 0 percent by weight to about 5 percent by weight, preferably about 0.5 percent by weight ascorbyl palmitate, from about 0.01 percent by weight to about 1.0 percent by weight, preferably about 0.1 percent by weight of one or a mixture of pharmaceutically acceptable preservatives and pharmaceutically acceptable flavors and sweetening agents.

The edible non-polar oil utilized in the emulsions of the present invention can be any pharmaceutically acceptable oil which is non-polar in nature, such as, for example, mineral oil, U.S.P. Likewise, an edible liquid, non-polar ester of an unsaturated fatty acid or mixtures of such esters can be utilized. A preferred preparation of this type is a mixture of mono- and di-glycerides of 16 to 18 carbon atom unsaturated fatty acids marketed under the trademark Atmos 300 by ICI, Inc., Wilmington, Delaware. Although the sorbitol may be obtained in dry form and formed into aqueous solution for incorporation into the emulsions of the present invention, the use of commercially available solutions is preferred. A particularly preferred preparation is a Sorbitol Solution, U.S.P., a 70 percent by weight solution available, for example, under the trademark Sorbo from ICI United States, Inc., Wilmington, Delaware.

While Polysorbate 80, N.F., i.e., polyoxyethylene (20) sorbitan monoleate, is the preferred pharmaceutically acceptable surfactant in the emulsions of the subject invention, other hydrophilic pharmaceutically acceptable surfactants which generally conform to the National Formulary monograph can be used as well. The bentonite utilized in the practice of the subject invention can be any purified pharmaceutical bentonite such as would conform to the monograph of the National Formulary. A preferred purified bentonite is marketed under the trademark Albagel 4444 by Whittaker, Clark and Daniels, Morristown, New Jersey.

The potassium chloride is added to the emulsions of the subject invention in the form of an aqueous solution. In effect, sufficient water is utilized to achieve solution of the desired amount of potassium chloride. Conveniently, a 25 percent by weight aqueous solution is utilized. While lecithin and ascorbyl palmitate may be omitted from the emulsions of the present invention, it is generally preferred that they be present, particularly ascorbyl palmitate which functions in a manner not entirely understood to stabilize the emulsion.

The pharmaceutically acceptable preservatives utilized in the novel emulsions of the present invention are those commonly recognized in the pharmaceutical compounding arts, such as, for example, methylparaben, propylparaben, sorbic acid, sodium benzoate and the like. While, generally, a variety of pharmaceutically acceptable flavoring and sweetening agents may be added to the emulsions of the subject invention, it has been found in extensive taste testing that an artifical banana flavor is preferable to produce an emulsion effectively masking the taste of potassium chloride.

It has been found in accordance with the present invention that the ratios of certain of the components of the herein disclosed water-in-oil emulsions must be within certain ranges. Thus, the ratio of the edible liquid, non-polar esters of unsaturated fatty acids to sorbitol wherein sorbitol is considered as a 70 percent by weight aqueous solution should be, on a volume-to-volume basis, from about 1:5 to about 1:20, preferably about 1:9. Further, the ratio of polysorbate 80 to purified bentonite should not exceed about 1:1 on a weight basis.

The novel water-in-oil emulsions of the present invention are prepared in accordance with techniques conventional to the pharmaceutical compounding arts. In general, the bentonite is well hydrated in water and an aqueous solution of potassium chloride containing the preservatives thoroughly mixed therewith. The polysorbate 80 is then added thereto and the mixture warmed to, e.g., about 70° C., to achieve homogeneity. The warm mixture is then slowly added to the oil phase to which suitable flavors and sweeteners, e.g. saccharin, have been added with high speed mixing and the resulting emulsion slowly cooled to room temperature with continued mixing. Wherein ascorbyl palmitate is present, it is initially added to the oil phase which has been warmed sufficiently to effect solution. The lecithin, where it is present, is then added with mixing to form the final emulsion.

The emulsions thus-formed have been found to be clearly preferable in taste to the liquid potassium chloride preparations commercially available against which it was tested. In addition, the emulsions of the present invention are stable, possess good bioavailability of potassium chloride and exhibit a uniform release of potassium chloride which is not as rapid as said commercial liquid preparation.

EXAMPLE 1

A water-in-oil emulsion was prepared from the following formulation:

| Ingredient | Amount |
| --- | --- |
| Atmos 300* | 20.00 ml. |
| Sorbitol Solution USP | 180.00 ml. |
| Purified Bentonite | 10.00 g. |
| Polysorbate 80 | 3.00 g. |
| Mineral Oil | 200.00 ml. |
| Potassium Chloride | 102.00 g. |
| Saccharin | 1.35 g. |
| Artificial Banana Flavor | 3.00 ml. |
| Methylparaben | 0.80 g. |
| Propylparaben | 0.20 g. |
| Distilled Water q.s. ad | 1000.00 ml. |

*Mixture of mono- and di-glycerides of 16–18 carbon atom unsaturated fatty acids. ICI, Inc. Wilmington, Delaware.

In a suitable vessel equiped with an agitator, the Atmos 300 was combined with the mineral oil, flavor, and saccharin with agitation until homogeneous. The Sorbitol Solution USP was then added slowly to the mixture with constant high shear mixing.

In a separate vessel the purified bentonite was hydrated in 100 ml. of distilled water with high speed mixing. The potassium chloride was dissolved in sufficient distilled water to yield a 25 percent by weight solution and added to the hydrated bentonite with high speed mixing. The resulting mixture was allowed to stand for 30 minutes. The Polysorbate 80 was dispersed in 10 ml. of hot distilled water and then added to the bentonite potassium chloride mixture with agitation. The methylparaben and propylparaben were added to the resulting dispersion, and it was then heated to 70° C. with agitation.

The bentonite/potassium chloride suspension was added slowly to the Atmos 300/sorbitol dispersion with high speed mixing. The resulting emulsion was than slowly cooled to room temperature with constant stirring. The resulting viscous emulsion was then packaged in suitable containers at room temperature.

EXAMPLE 2

An emulsion was prepared in accordance with the procedure of Example 1 with the addition of 3.0 g. ascorbyl palmitate. The ascorbyl palmitate was added with stirring to the mineral oil combined with the Atmos 300 and the mixture heated to dissolve the ascorbyl palmitate.

EXAMPLE 3

An emulsion was prepared in accordance with the procedure of Example 1 with the addition of 3.0 g of lecithin.* The lecithin was added to the final emulsion with high speed stirring after the addition of the Atmos 300/sorbitol mixture was completed.

*Alcolec S, American Lecithin Co., Woodside, New York.

I claim:
1. An improved potassium chloride water-in-oil emulsion comprising, per liter:
   (a) from about 500 ml. to about 700 ml. water;
   (b) from about 8 percent to about 24 percent weight to volume sorbitol;

(c) from about 100 ml. to about 300 ml. of mineral oil, U.S.P.;
(d) from about 5 percent to about 15 percent by weight potassium chloride;
(e) from about 1 percent to about 5 percent weight to volume purified bentonite;
(f) from about 10 ml. to about 30 ml. of a mixture of monoglycerides and diglycerides of 16 to 18 carbon atom unsalurated fatty acids;
(g) from about 0.01 percent to about 1.0 percent weight to volume polysorbate 80;
(h) from 0 to about 3 percent by weight lecithin;
(i) from 0 to about 5 percent by weight ascorbyl palmitate; and
(j) pharmaceutically acceptable preservatives, flavors and sweetening agents.

2. An emulsion in accordance with claim 1 wherein said ingredient (b) is Sorbitol Solution, U.S.P., and the ratio of said ingredient (f) to said ingredient (b) on a volume-to-volume basis is from about 1:5 to about 1:20.

3. An emulsion in accordance with claim 2 wherein the ratio of said ingredient (f) to said ingredient (b) is 1:9.

4. An emulsion in accordance with claim 1 wherein said emulsion comprises, per liter;
(a) about 600 ml. water;
(b) about 16 percent weight to volume sorbitol;
(c) about 200 ml. of mineral oil, U.S.P.;
(d) about 10 percent by weight potassium chloride;
(e) about 1 percent weight to volume purified bentonite;
(f) about 20 ml. of a mixture of monoglycerides and diglycerides of 16 to 18 carbon atom unsaturated fatty acids;
(g) about 0.3 percent weight to volume polysorbate 80;
(h) from 0 to about 3 percent by weight lecithin;
(i) from 0 to about 5 percent by weight ascorbyl palmitate; and
(j) pharmaceutically acceptable preservatives, flavors and sweetening agents.

5. An emulsion in accordance with claim 1 wherein said pharmaceutically acceptable preservatives, flavors and sweetening agents comprises from about 0.01 to about 1.0 percent by weight of said emulsion.

6. An emulsion in accordance with claims 1 or 4 wherein said emulsion contains about 0.5 percent by weight lecithin.

7. An emulsion in accordance with claims 1 or 4, wherein said emulsion contains about 0.5 percent by weight ascorbyl palmitate.

* * * * *